(12) United States Patent
Stats et al.

(10) Patent No.: US 10,463,845 B2
(45) Date of Patent: Nov. 5, 2019

(54) LOW-PROFILE ACCESS PORT

(71) Applicant: C. R. Bard, Inc., Murray Hill, NJ (US)

(72) Inventors: Jason R. Stats, Layton, UT (US); Bret Hamatake, Grantsville, UT (US); Dwight T. Hibdon, Park City, UT (US); Kelly J. Christian, Draper, UT (US)

(73) Assignee: C.R. Bard, Inc., Murray Hill, NJ (US)

( * ) Notice: Subject to any disclaimer, the term of this patent is extended or adjusted under 35 U.S.C. 154(b) by 601 days.

(21) Appl. No.: 14/162,113

(22) Filed: Jan. 23, 2014

(65) Prior Publication Data

US 2014/0207086 A1 Jul. 24, 2014

Related U.S. Application Data

(60) Provisional application No. 61/755,913, filed on Jan. 23, 2013.

(51) Int. Cl.
*A61M 39/02* (2006.01)

(52) U.S. Cl.
CPC . *A61M 39/0208* (2013.01); *A61M 2039/0211* (2013.01); *A61M 2039/0232* (2013.01);
(Continued)

(58) Field of Classification Search
CPC ...... A61M 39/0208; A61M 2039/0211; A61M 2039/0232; A61M 2039/0235;
(Continued)

(56) References Cited

U.S. PATENT DOCUMENTS 3,951,147 A 4/1976 Tucker et al.
4,184,489 A 1/1980 Burd
(Continued)

FOREIGN PATENT DOCUMENTS

CA 1261698 A1 9/1989
CA 2318089 A1 7/1999
(Continued)

OTHER PUBLICATIONS

PCT/US2014/012721 filed Jan. 23, 2014 International Search Report and Written Opinion dated Apr. 14, 2014.
(Continued)

*Primary Examiner* — Bhisma Mehta
*Assistant Examiner* — Larry R. Wilson
(74) *Attorney, Agent, or Firm* — Rutan & Tucker, LLP

(57) ABSTRACT

A low-profile access port for subcutaneous implantation within the body of a patient is disclosed. The access port includes a receiving cup that provides a relatively large subcutaneous target to enable a catheter-bearing needle to access the port without difficulty. In addition, the access port includes a valve/seal assembly to permit pressurized fluid injection through the port while preventing backflow. In one embodiment, therefore, a low-profile access port comprises a body including a conduit with an inlet port at a proximal end thereof, and a receiving cup. The receiving cup is concavely shaped to direct a catheter-bearing needle into the conduit via the inlet port. The receiving cup is oriented substantially toward a skin surface when subcutaneously implanted within the patient to ease needle impingement thereon. A valve/seal assembly disposed in the conduit enables passage of the catheter therethrough while preventing fluid backflow.

23 Claims, 15 Drawing Sheets

(52) U.S. Cl.
CPC ............... *A61M 2039/0235* (2013.01); *A61M 2039/0238* (2013.01); *Y10T 29/49826* (2015.01)

(58) Field of Classification Search
CPC ...... A61M 2039/0238; A61M 39/0247; A61M 39/04; A61M 25/09041; A61M 39/02; A61M 2039/0205; A61M 2039/0258; A61M 2039/0273; A61M 2039/0276; A61M 2039/0279; A61M 2039/042; A61M 2039/1027; Y01T 29/49826
See application file for complete search history.

(56) References Cited

U.S. PATENT DOCUMENTS

| | | | |
|---|---|---|---|
| 4,222,374 A | 9/1980 | Sampson et al. |
| 4,400,169 A | 8/1983 | Stephen |
| 4,447,237 A | 5/1984 | Frisch et al. |
| 4,496,349 A | 1/1985 | Cosentino |
| 4,543,088 A | 9/1985 | Bootman et al. |
| 4,559,039 A | 12/1985 | Ash et al. |
| 4,569,675 A | 2/1986 | Prosl et al. |
| 4,673,394 A | 6/1987 | Fenton, Jr. et al. |
| 4,692,146 A | 9/1987 | Hilger |
| 4,695,273 A | 9/1987 | Brown |
| 4,704,103 A | 11/1987 | Stober et al. |
| 4,710,174 A | 12/1987 | Moden et al. |
| 4,762,517 A | 8/1988 | McIntyre et al. |
| 4,767,410 A | 8/1988 | Moden et al. |
| 4,772,270 A | 9/1988 | Wiita et al. |
| 4,772,276 A | 9/1988 | Wiita et al. |
| 4,778,452 A | 10/1988 | Moden et al. |
| 4,790,826 A | 12/1988 | Elftman |
| 4,802,885 A | 2/1989 | Weeks et al. |
| 4,804,054 A | 2/1989 | Howson et al. |
| 4,820,273 A | 4/1989 | Reinicke |
| 4,861,341 A | 8/1989 | Woodburn |
| 4,886,501 A | 12/1989 | Johnston et al. |
| 4,892,518 A | 1/1990 | Cupp et al. |
| 4,897,081 A | 1/1990 | Poirier et al. |
| 4,904,241 A | 2/1990 | Bark |
| 4,915,690 A | 4/1990 | Cone et al. |
| 4,929,236 A | 5/1990 | Sampson |
| 4,963,133 A | 10/1990 | Whipple |
| 4,978,338 A | 12/1990 | Melsky et al. |
| 5,013,298 A | 5/1991 | Moden et al. |
| 5,041,098 A | 8/1991 | Loiterman et al. |
| 5,045,060 A | 9/1991 | Melsky et al. |
| 5,045,064 A | 9/1991 | Idriss |
| 5,053,013 A | 10/1991 | Ensminger et al. |
| 5,057,084 A | 10/1991 | Ensminger et al. |
| 5,084,015 A | 1/1992 | Moriuchi |
| 5,090,954 A | 2/1992 | Geary |
| 5,108,377 A | 4/1992 | Cone et al. |
| 5,137,529 A | 8/1992 | Watson et al. |
| 5,147,321 A | 9/1992 | Slonina et al. |
| 5,147,483 A | 9/1992 | Melsky et al. |
| 5,158,547 A | 10/1992 | Doan et al. |
| 5,167,633 A | 12/1992 | Mann et al. |
| 5,167,638 A | 12/1992 | Felix et al. |
| 5,171,228 A | 12/1992 | McDonald |
| 5,178,612 A | 1/1993 | Fenton, Jr. |
| 5,180,365 A | 1/1993 | Ensminger et al. |
| 5,185,003 A | 2/1993 | Brethauer |
| 5,201,715 A | 4/1993 | Masters |
| 5,203,771 A | 4/1993 | Melker et al. |
| 5,213,574 A | 5/1993 | Tucker |
| D337,637 S | 7/1993 | Tucker |
| 5,226,879 A | 7/1993 | Ensminger et al. |
| 5,263,930 A | 11/1993 | Ensminger |
| 5,266,071 A | 11/1993 | Elftman |
| 5,281,199 A | 1/1994 | Ensminger et al. |
| 5,281,205 A | 1/1994 | McPherson |
| 5,318,545 A | 6/1994 | Tucker |
| 5,336,194 A | 8/1994 | Polaschegg et al. |
| 5,350,360 A | 9/1994 | Ensminger et al. |
| 5,356,381 A * | 10/1994 | Ensminger ........ A61M 39/0208 604/181 |
| 5,360,407 A | 11/1994 | Leonard et al. |
| 5,387,192 A | 2/1995 | Glantz et al. |
| 5,395,324 A | 3/1995 | Hinrichs et al. |
| 5,399,168 A | 3/1995 | Wadsworth, Jr. et al. |
| 5,405,325 A | 4/1995 | Labs |
| 5,417,656 A | 5/1995 | Ensminger et al. |
| 5,421,814 A | 6/1995 | Geary |
| 5,423,334 A | 6/1995 | Jordan |
| 5,476,451 A | 12/1995 | Ensminger et al. |
| 5,503,630 A | 4/1996 | Ensminger et al. |
| 5,514,103 A | 5/1996 | Srisathapat et al. |
| 5,520,643 A | 5/1996 | Ensminger et al. |
| 5,527,277 A | 6/1996 | Ensminger et al. |
| 5,527,278 A | 6/1996 | Ensminger et al. |
| 5,531,684 A | 7/1996 | Ensminger et al. |
| 5,542,923 A | 8/1996 | Ensminger et al. |
| 5,554,117 A | 9/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,575,770 A | 11/1996 | Melsky et al. |
| 5,578,070 A | 11/1996 | Utterberg |
| 5,607,393 A | 3/1997 | Ensminger et al. |
| 5,613,945 A | 3/1997 | Cai et al. |
| 5,620,419 A | 4/1997 | Lui et al. |
| 5,632,729 A | 5/1997 | Cai et al. |
| 5,647,855 A | 7/1997 | Trooskin |
| 5,695,490 A | 12/1997 | Flaherty et al. |
| 5,702,363 A | 12/1997 | Flaherty |
| 5,713,858 A | 2/1998 | Heruth et al. |
| 5,718,682 A | 2/1998 | Tucker |
| 5,725,507 A | 3/1998 | Petrick |
| 5,741,228 A * | 4/1998 | Lambrecht ........ A61M 39/0208 251/149.3 |
| 5,743,873 A | 4/1998 | Cai et al. |
| 5,758,667 A | 6/1998 | Slettenmark |
| 5,769,823 A | 6/1998 | Otto |
| 5,792,104 A * | 8/1998 | Speckman ........ A61M 39/0208 604/175 |
| 5,810,789 A | 9/1998 | Powers et al. |
| 5,833,654 A | 11/1998 | Powers et al. |
| 5,848,989 A | 12/1998 | Villani |
| 5,906,596 A | 5/1999 | Tallarida |
| 5,908,414 A | 6/1999 | Otto et al. |
| 5,913,998 A | 6/1999 | Butler et al. |
| 5,925,017 A | 7/1999 | Kriesel et al. |
| 5,931,829 A | 8/1999 | Burbank et al. |
| 5,944,688 A | 8/1999 | Lois |
| 5,947,953 A | 9/1999 | Ash et al. |
| 5,951,512 A | 9/1999 | Dalton |
| 5,954,687 A | 9/1999 | Baudino |
| 5,954,691 A | 9/1999 | Prosl |
| 5,968,011 A | 10/1999 | Larsen et al. |
| 5,989,206 A | 11/1999 | Prosl et al. |
| 5,989,216 A | 11/1999 | Johnson et al. |
| 5,989,239 A | 11/1999 | Finch et al. |
| 6,007,516 A | 12/1999 | Burbank et al. |
| 6,013,051 A | 1/2000 | Nelson |
| 6,013,058 A | 1/2000 | Prosl et al. |
| 6,022,335 A | 2/2000 | Ramadan |
| 6,039,712 A | 3/2000 | Fogarty et al. |
| 6,042,569 A | 3/2000 | Finch, Jr. et al. |
| 6,053,901 A | 4/2000 | Finch, Jr. et al. |
| 6,056,717 A | 5/2000 | Finch et al. |
| 6,086,555 A | 7/2000 | Eliasen et al. |
| 6,090,067 A | 7/2000 | Carter |
| 6,090,068 A | 7/2000 | Chanut |
| 6,102,884 A | 8/2000 | Squitieri |
| 6,120,492 A | 9/2000 | Finch et al. |
| 6,190,349 B1 | 2/2001 | Ash et al. |
| 6,190,352 B1 | 2/2001 | Haarala et al. |
| 6,206,851 B1 | 3/2001 | Prosl |
| 6,213,973 B1 | 4/2001 | Eliasen et al. |
| D445,175 S | 7/2001 | Bertheas |

(56) References Cited

U.S. PATENT DOCUMENTS

| | | |
|---|---|---|
| 6,287,293 B1 | 9/2001 | Jones et al. |
| 6,332,874 B1 | 12/2001 | Eliasen et al. |
| 6,350,251 B1 | 2/2002 | Prosl et al. |
| 6,352,521 B1 | 3/2002 | Prosl |
| 6,398,764 B1 | 6/2002 | Finch, Jr. et al. |
| 6,436,084 B1 | 8/2002 | Finch et al. |
| 6,438,397 B1 | 8/2002 | Bosquet et al. |
| 6,459,917 B1 | 10/2002 | Gowda et al. |
| 6,478,783 B1 | 11/2002 | Moorehead |
| 6,482,197 B2 | 11/2002 | Finch et al. |
| 6,494,867 B1 | 12/2002 | Elver et al. |
| 6,506,182 B2 | 1/2003 | Estabrook et al. |
| 6,527,754 B1 | 3/2003 | Tallarida et al. |
| 6,540,717 B2 | 4/2003 | Sherry |
| 6,582,409 B1 | 6/2003 | Squitieri |
| 6,607,504 B2 | 8/2003 | Haarala et al. |
| 6,620,118 B1 | 9/2003 | Prosl et al. |
| 6,695,832 B2 | 2/2004 | Schon et al. |
| 6,699,218 B2 | 3/2004 | Flaherty et al. |
| 6,719,749 B1 | 4/2004 | Schweikert et al. |
| 6,726,711 B1 | 4/2004 | Langenbach et al. |
| 6,758,841 B2 | 7/2004 | Haarala et al. |
| 6,783,522 B2 | 8/2004 | Fischell |
| 6,852,106 B2 | 2/2005 | Watson et al. |
| 6,881,211 B2 | 4/2005 | Schweikert et al. |
| 6,929,631 B1 | 8/2005 | Brugger et al. |
| 6,960,185 B2 | 11/2005 | Adaniya et al. |
| 6,962,580 B2 | 11/2005 | Adams et al. |
| 6,997,914 B2 | 2/2006 | Smith et al. |
| 7,018,374 B2 | 3/2006 | Schon et al. |
| 7,056,316 B1 | 6/2006 | Burbank et al. |
| 7,070,591 B2 | 7/2006 | Adams et al. |
| 7,083,648 B2 | 8/2006 | Yu et al. |
| 7,108,686 B2 | 9/2006 | Burke et al. |
| 7,131,962 B1 * | 11/2006 | Estabrook .......... A61M 39/0208 604/93.01 |
| 7,223,257 B2 | 5/2007 | Shubayev et al. |
| 7,261,705 B2 | 8/2007 | Edoga et al. |
| 7,311,702 B2 | 12/2007 | Tallarida et al. |
| 7,322,953 B2 | 1/2008 | Redinger |
| D562,443 S | 2/2008 | Zinn et al. |
| 7,347,843 B2 | 3/2008 | Adams et al. |
| 7,351,233 B2 | 4/2008 | Parks |
| 7,396,359 B1 | 7/2008 | Derowe et al. |
| D574,950 S | 8/2008 | Zawacki et al. |
| D578,203 S | 10/2008 | Bizup |
| 7,445,614 B2 | 11/2008 | Bunodiere et al. |
| D582,032 S | 12/2008 | Bizup et al. |
| 7,497,850 B2 | 3/2009 | Halili |
| D612,479 S | 3/2010 | Zawacki et al. |
| 7,699,821 B2 | 4/2010 | Nowak |
| 7,704,225 B2 | 4/2010 | Kantrowitz |
| 7,708,722 B2 | 5/2010 | Glenn |
| 7,713,251 B2 | 5/2010 | Tallarida et al. |
| 7,731,680 B2 | 6/2010 | Patton |
| 7,762,999 B2 | 7/2010 | Byrum |
| 7,824,365 B2 | 11/2010 | Haarala et al. |
| 7,846,139 B2 | 12/2010 | Zinn et al. |
| 7,850,666 B2 | 12/2010 | Schon et al. |
| 7,909,804 B2 | 3/2011 | Stats |
| 7,959,615 B2 | 6/2011 | Stats et al. |
| 7,972,315 B2 | 7/2011 | Birk et al. |
| 7,981,094 B2 | 7/2011 | Chelak |
| D650,475 S | 12/2011 | Smith et al. |
| 8,075,536 B2 | 12/2011 | Gray et al. |
| 8,079,990 B2 | 12/2011 | Powley et al. |
| 8,147,455 B2 | 4/2012 | Butts et al. |
| 8,152,792 B1 | 4/2012 | Komel |
| 8,257,325 B2 | 9/2012 | Schweikert et al. |
| 8,277,425 B2 | 10/2012 | Girard et al. |
| 8,328,768 B2 | 12/2012 | Quigley et al. |
| 8,337,464 B2 | 12/2012 | Young et al. |
| 8,337,465 B2 | 12/2012 | Young et al. |
| 8,337,470 B2 | 12/2012 | Prasad et al. |
| 8,343,108 B2 | 1/2013 | Rosenberg et al. |
| 8,364,230 B2 | 1/2013 | Simpson et al. |
| 8,377,034 B2 | 2/2013 | Tallarida et al. |
| 8,425,416 B2 | 4/2013 | Brister et al. |
| 8,425,476 B2 | 4/2013 | Glenn |
| 8,480,560 B2 | 7/2013 | Vendely |
| 8,550,981 B2 | 10/2013 | Woodruff et al. |
| 8,574,204 B2 | 11/2013 | Boume et al. |
| RE44,639 E | 12/2013 | Squitieri |
| 8,622,980 B2 | 1/2014 | Zinn |
| 8,690,815 B2 | 4/2014 | Porter et al. |
| 8,690,816 B2 | 4/2014 | Dakin et al. |
| 8,738,151 B2 | 5/2014 | Nelson |
| 8,979,806 B2 | 3/2015 | Saab |
| 9,033,931 B2 * | 5/2015 | Young .......... A61B 17/0057 604/175 |
| 9,061,129 B2 | 6/2015 | Lauer |
| 9,072,880 B2 | 7/2015 | Phillips et al. |
| 9,072,881 B2 | 7/2015 | Dalton et al. |
| 9,078,982 B2 | 7/2015 | Lane et al. |
| 9,089,395 B2 | 7/2015 | Honaryar |
| 9,095,665 B2 | 8/2015 | Pages et al. |
| 9,138,563 B2 | 9/2015 | Glenn |
| 9,168,365 B2 | 10/2015 | Bourne et al. |
| 9,174,037 B2 | 11/2015 | Schutz et al. |
| 9,179,901 B2 | 11/2015 | Young et al. |
| 9,180,248 B2 | 11/2015 | Moberg et al. |
| 9,474,888 B2 | 10/2016 | Wiley et al. |
| 9,579,496 B2 | 2/2017 | Evans et al. |
| 9,987,467 B2 | 6/2018 | Jochum |
| 10,207,095 B2 | 2/2019 | Barron et al. |
| 10,272,236 B2 | 4/2019 | Davey |
| 2001/0041870 A1 | 11/2001 | Gillis et al. |
| 2001/0056266 A1 | 12/2001 | Tallarida et al. |
| 2003/0023208 A1 | 1/2003 | Osypka et al. |
| 2003/0181878 A1 | 9/2003 | Tallarida et al. |
| 2004/0054352 A1 | 3/2004 | Adams et al. |
| 2004/0073196 A1 | 4/2004 | Adams et al. |
| 2004/0199129 A1 | 10/2004 | DiMatteo |
| 2004/0204692 A1 | 10/2004 | Eliasen |
| 2004/0254536 A1 | 12/2004 | Conlon et al. |
| 2004/0254537 A1 | 12/2004 | Conlon et al. |
| 2005/0075614 A1 | 4/2005 | Bunodiere et al. |
| 2005/0113806 A1 | 5/2005 | De Carvalho et al. |
| 2005/0131352 A1 | 6/2005 | Conlon et al. |
| 2005/0148956 A1 | 7/2005 | Conlon et al. |
| 2005/0148957 A1 | 7/2005 | Girard et al. |
| 2005/0171502 A1 | 8/2005 | Daly et al. |
| 2005/0209573 A1 | 9/2005 | Brugger et al. |
| 2005/0256451 A1 | 11/2005 | Adams et al. |
| 2005/0277899 A1 | 12/2005 | Conlon et al. |
| 2006/0084929 A1 | 4/2006 | Eliasen |
| 2006/0089619 A1 | 4/2006 | Ginggen |
| 2006/0100592 A1 | 5/2006 | Eliasen |
| 2006/0173424 A1 | 8/2006 | Conlon |
| 2006/0178617 A1 | 8/2006 | Adams et al. |
| 2006/0178647 A1 | 8/2006 | Stats |
| 2006/0184142 A1 | 8/2006 | Schon et al. |
| 2006/0217659 A1 | 9/2006 | Patton |
| 2006/0217673 A1 | 9/2006 | Schulze et al. |
| 2006/0224129 A1 | 10/2006 | Beasley et al. |
| 2006/0247584 A1 | 11/2006 | Sheetz et al. |
| 2006/0264898 A1 | 11/2006 | Beasley et al. |
| 2006/0271012 A1 | 11/2006 | Canaud et al. |
| 2007/0049806 A1 | 3/2007 | Adams et al. |
| 2007/0073250 A1 | 3/2007 | Schneiter |
| 2007/0078391 A1 | 4/2007 | Wortley et al. |
| 2007/0078416 A1 | 4/2007 | Eliasen |
| 2007/0083156 A1 | 4/2007 | Muto et al. |
| 2007/0161958 A1 | 7/2007 | Glenn |
| 2007/0179456 A1 | 8/2007 | Glenn |
| 2007/0208313 A1 | 9/2007 | Conlon et al. |
| 2007/0219510 A1 | 9/2007 | Zinn et al. |
| 2007/0232997 A1 | 10/2007 | Glenn |
| 2007/0233017 A1 | 10/2007 | Zinn et al. |
| 2007/0233018 A1 | 10/2007 | Bizup et al. |
| 2007/0255234 A1 * | 11/2007 | Haase .......... A61M 5/14276 604/288.01 |
| 2007/0270770 A1 | 11/2007 | Bizup |
| 2007/0276344 A1 | 11/2007 | Bizup et al. |

(56) References Cited

U.S. PATENT DOCUMENTS

| | | |
|---|---|---|
| 2007/0282308 A1 | 12/2007 | Bell |
| 2008/0048855 A1 | 2/2008 | Berger |
| 2008/0086075 A1 | 4/2008 | Isik et al. |
| 2008/0108942 A1 | 5/2008 | Blister et al. |
| 2008/0114308 A1 | 5/2008 | di Palma et al. |
| 2008/0132946 A1 | 6/2008 | Mueller |
| 2008/0208236 A1 | 8/2008 | Hobbs et al. |
| 2008/0281279 A1 | 11/2008 | Hoendervoogt et al. |
| 2008/0319399 A1 | 12/2008 | Schweikert et al. |
| 2008/0319405 A1 | 12/2008 | Bizup |
| 2009/0024024 A1 | 1/2009 | Zinn |
| 2009/0024098 A1 | 1/2009 | Bizup et al. |
| 2009/0105688 A1 | 4/2009 | McIntyre et al. |
| 2009/0118683 A1 | 5/2009 | Hanson et al. |
| 2009/0156928 A1 | 6/2009 | Evans et al. |
| 2009/0192467 A1 | 7/2009 | Hansen et al. |
| 2009/0204074 A1 | 8/2009 | Powers et al. |
| 2009/0221976 A1 | 9/2009 | Linden |
| 2009/0259164 A1 | 10/2009 | Pages et al. |
| 2010/0042073 A1 | 2/2010 | Oster et al. |
| 2010/0121283 A1 | 5/2010 | Hamatake et al. |
| 2010/0298684 A1 | 11/2010 | Leach et al. |
| 2011/0118677 A1* | 5/2011 | Wiley ............... A61M 39/0208 604/288.01 |
| 2011/0257577 A1 | 10/2011 | Lane et al. |
| 2011/0264058 A1 | 10/2011 | Linden et al. |
| 2011/0319728 A1 | 12/2011 | Petisce et al. |
| 2012/0172711 A1 | 7/2012 | Kerr et al. |
| 2012/0283518 A1 | 11/2012 | Hart |
| 2013/0030348 A1 | 1/2013 | Lauer |
| 2013/0150767 A1 | 6/2013 | Tsyrulnykov et al. |
| 2013/0150811 A1 | 6/2013 | Horgan |
| 2015/0190622 A1 | 7/2015 | Saab |
| 2015/0196704 A1 | 7/2015 | Adler |
| 2015/0250933 A1 | 9/2015 | Kerkhoffs et al. |
| 2015/0258322 A1 | 9/2015 | Young et al. |
| 2015/0265280 A1 | 9/2015 | Blatter et al. |
| 2015/0273201 A1 | 10/2015 | Tallarida et al. |
| 2015/0290446 A1 | 10/2015 | Wiley et al. |
| 2015/0306300 A1 | 10/2015 | Phillips et al. |
| 2015/0327844 A1 | 11/2015 | Hong et al. |
| 2016/0001055 A1 | 1/2016 | Bourne et al. |
| 2018/0078751 A1 | 3/2018 | Fedor et al. |
| 2019/0232035 A1 | 8/2019 | Fedor et al. |

FOREIGN PATENT DOCUMENTS

| | | | |
|---|---|---|---|
| CA | 2551680 A1 | 7/2005 | |
| CN | 102271737 A | 12/2011 | |
| EP | 0229729 A2 | 7/1987 | |
| EP | 0366814 A1 | 5/1990 | |
| EP | 1056506 A1 | 12/2000 | |
| EP | 2948121 B1 | 11/2017 | |
| JP | H05-506591 A | 9/1993 | |
| JP | H07-148206 A | 6/1995 | |
| JP | H08-501008 A | 2/1996 | |
| JP | 2008-531226 A | 8/2008 | |
| WO | 1991/012838 A1 | 9/1991 | |
| WO | 1993005730 A1 | 4/1993 | |
| WO | 1994005246 A1 | 3/1994 | |
| WO | WO 9405246 A1 * | 3/1994 | ........ A61M 39/0208 |
| WO | 96/25196 A1 | 8/1996 | |
| WO | 1996029112 A1 | 9/1996 | |
| WO | 1997001370 A1 | 1/1997 | |
| WO | 1997006845 A1 | 2/1997 | |
| WO | 1998017337 A1 | 4/1998 | |
| WO | 1999034859 A1 | 7/1999 | |
| WO | 1999042166 A1 | 8/1999 | |
| WO | 2000033901 A1 | 6/2000 | |
| WO | 2000044424 | 8/2000 | |
| WO | 2000053245 | 9/2000 | |
| WO | 2001026713 | 4/2001 | |
| WO | 01/80926 A2 | 11/2001 | |
| WO | 2002038460 | 5/2002 | |
| WO | 2002066595 | 8/2002 | |
| WO | 2003066126 | 8/2003 | |
| WO | 2004004800 A2 | 1/2004 | |
| WO | 2004071555 A2 | 8/2004 | |
| WO | 2004091434 A2 | 10/2004 | |
| WO | 2004093970 A1 | 11/2004 | |
| WO | 2005068009 A1 | 7/2005 | |
| WO | 2006064753 A1 | 6/2006 | |
| WO | 2006078915 A2 | 7/2006 | |
| WO | 2006096686 A1 | 9/2006 | |
| WO | 2006116438 A2 | 11/2006 | |
| WO | 2006130133 A1 | 12/2006 | |
| WO | 2006134100 A1 | 12/2006 | |
| WO | 2007079024 A2 | 7/2007 | |
| WO | 2007082003 A2 | 7/2007 | |
| WO | 2007087460 A2 | 8/2007 | |
| WO | 2007092210 A1 | 8/2007 | |
| WO | 2007094898 A2 | 8/2007 | |
| WO | 2007098771 A2 | 9/2007 | |
| WO | 2007109164 A2 | 9/2007 | |
| WO | 2007126645 A2 | 11/2007 | |
| WO | 2007136538 A2 | 11/2007 | |
| WO | 2008048361 A1 | 4/2008 | |
| WO | 2008063226 A2 | 5/2008 | |
| WO | 2008140901 A1 | 11/2008 | |
| WO | 2008157763 A1 | 12/2008 | |
| WO | 2009002839 A1 | 12/2008 | |
| WO | 2009012385 A1 | 1/2009 | |
| WO | 2009035582 A1 | 3/2009 | |
| WO | 2009046439 A2 | 4/2009 | |
| WO | 2009108669 A1 | 9/2009 | |
| WO | 2012064881 A2 | 5/2012 | |
| WO | 2014017986 A1 | 1/2014 | |
| WO | 2014116810 A1 | 7/2014 | |
| WO | 2015179862 A1 | 11/2015 | |

OTHER PUBLICATIONS

Canaud, B. et. al. "Dialock: a new vascular access device for extracorporeal renal replacement therapy. Preliminary clinical results" (Mar. 1999).

Goldstein, D. J. et. al. "Implantable Left Ventricular Assist Devices" (Nov. 19, 1998).

Moran, J. E. "Subcutaneous Vascular Access Devices" (Nov. 2001).

Rosenblatt, M. et. al. "Efficacy and Safety Results with the LifeSite Hemodialysis Access System versus the Tesio-Cath Hemodialysis Catheter at 12 Months" (Mar. 2006).

Sandhu, J. Dialysis Ports: A New Totally Implantable Option for Hemodialysis Access (Jun. 2002).

CN 201480005902.2 filed Jul. 23, 2015 Office Action dated Jul. 19, 2016.

EP 14743846.9 filed Aug. 12, 2015 Extended European Search Report dated Oct. 10, 2016.

CN 201480005902.2 filed Jul. 23, 2015 Office Action dated Jan. 20, 2016.

CN 201480005902.2 filed Jul. 23, 2015 Office Action dated May 12, 2017.

EP 14743846.9 filed Aug. 12, 2015 Intent to Grant dated Jun. 26, 2017.

JP 2015-555266 filed Jul. 22, 2015 Office Action dated Oct. 12, 2017.

PCT/US2017/061179 filed Nov. 10, 2017 International Search Report and Written Opinion dated Jan. 22, 2018.

JP 2015-555266 filed Jul. 22, 2015 Office Action dated May 2, 2018.

U.S. Appl. No. 29/616,511, filed Sep. 6, 2017 Notice of Allowance dated Aug. 8, 2019.

* cited by examiner

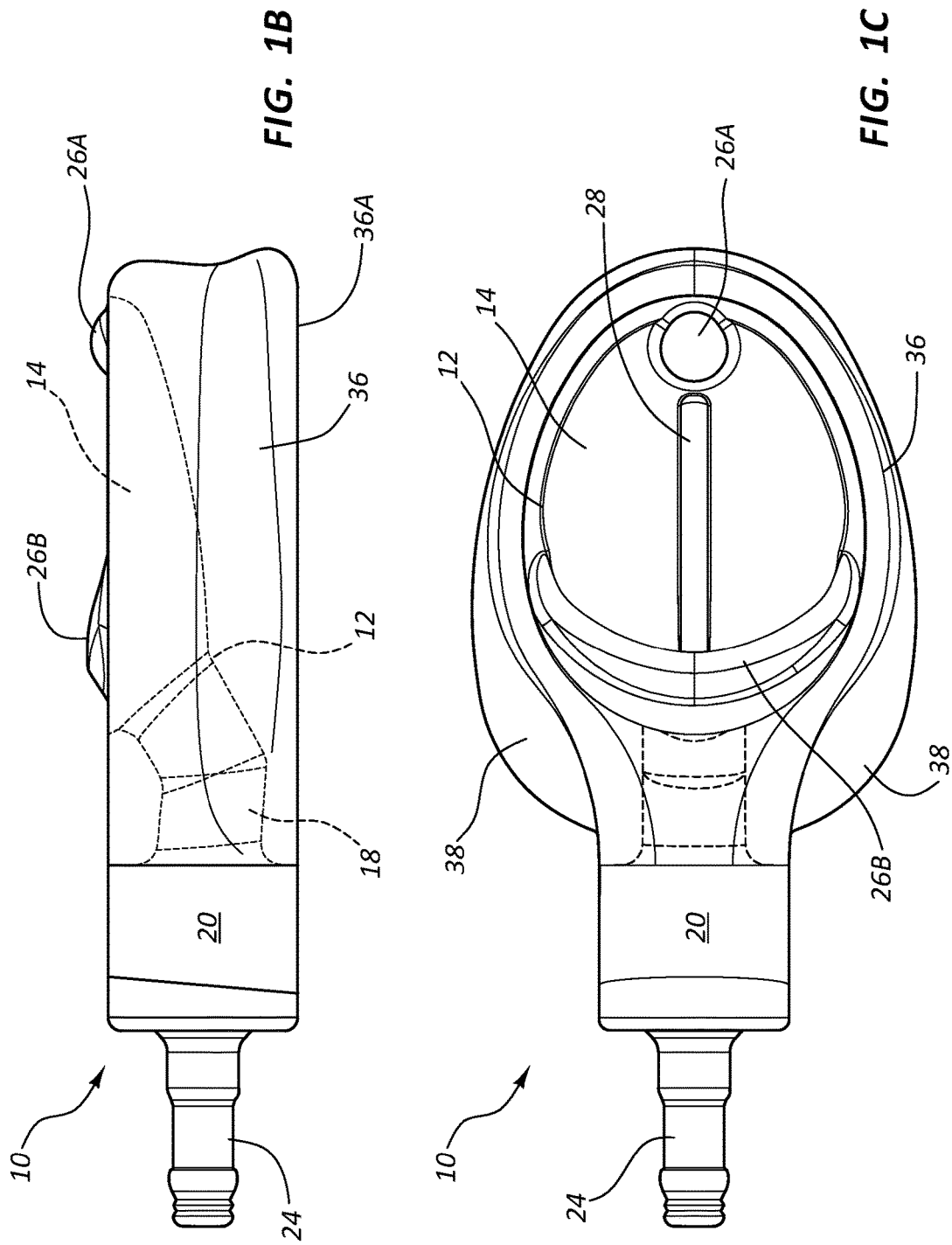

LOW-PROFILE ACCESS PORT

CROSS-REFERENCE TO RELATED APPLICATIONS

This application claims the benefit of U.S. Provisional Patent Application No. 61/755,913, filed Jan. 23, 2013, and titled "Low Profile Access Port," which is incorporated herein by reference in its entirety.

BRIEF SUMMARY

Briefly summarized, embodiments of the present invention are directed to a low-profile access port for subcutaneous implantation within the body of a patient. The access port includes a receiving cup that provides a relatively large subcutaneous target to enable a catheter-bearing needle to access the port without difficulty. In addition, the access port includes a valve/seal assembly to permit pressurized fluid injection through the port while preventing backflow.

In one embodiment, therefore, a low-profile access port comprises a body including a conduit with an inlet port at a proximal end thereof, and a receiving cup. The receiving cup is concavely shaped to direct a catheter-bearing needle into the conduit via the inlet port. The receiving cup is oriented substantially toward a skin surface when subcutaneously implanted within the patient to ease needle impingement thereon. A valve/seal assembly disposed in the conduit enables passage of the catheter therethrough while preventing fluid backflow.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 1A-1E show various views of an access port according to one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to an access port for subcutaneous implantation within the body of a patient. The implanted access port is transcutaneously accessible by a catheter-bearing needle, such as a peripheral intravenous ("PIV") catheter, so as to place the PIV catheter into fluid communication with the access port. A fluid outlet of the access port is operably connected to an in-dwelling catheter disposed within the vasculature of a patient, in one embodiment, to enable the infusion into and/or removal of fluids from the patient's vasculature to take place via the PIV catheter.

In accordance with one embodiment, the access port defines a low profile so as to facilitate ease of placement within the subcutaneous tissue of the patient. Further, the access port is configured to provide a relatively large subcutaneous target to enable the PIV catheter or other suitable catheter-bearing needle to access the port without difficulty. In addition, the access port includes a valve/seal assembly to permit the injection of fluids through the access port at a relatively high flow rate, such as about 5 ml per second at a pressure of about 300 psi (also referred to herein as "power injection"). Possible applications for the access port described herein include administration of medicaments and other fluids to the patient, pheresis, fluid aspiration, etc.

Figure 1A:
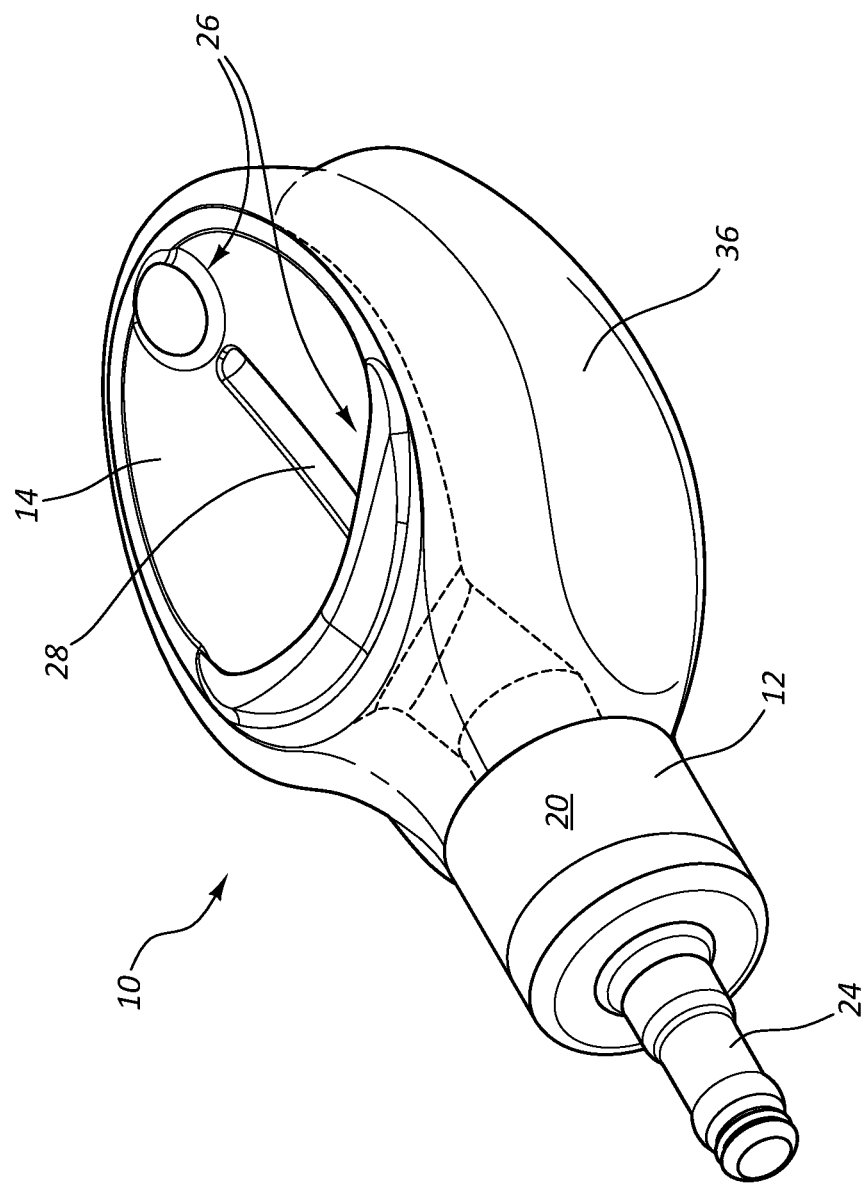
Figure 1D:
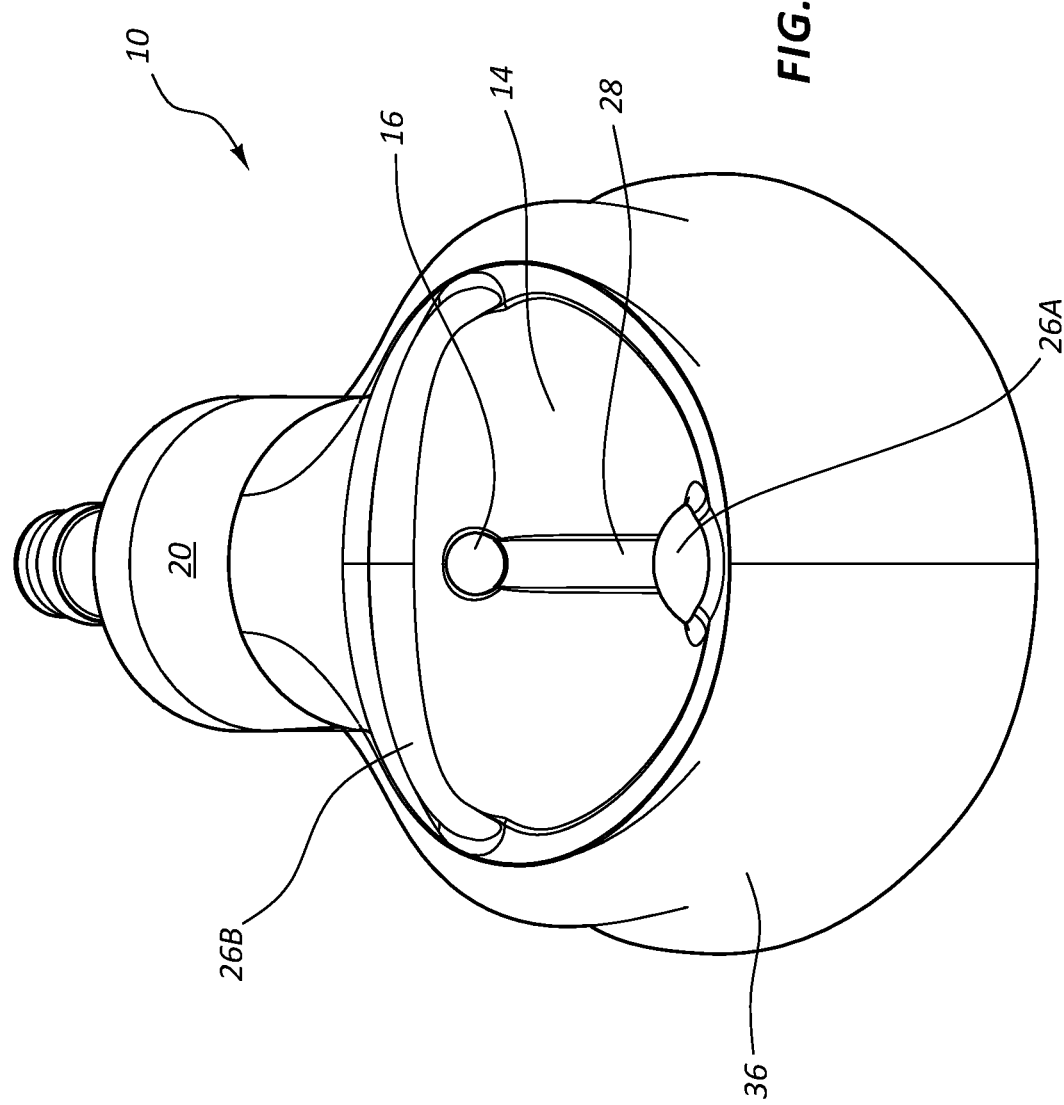
Figure 1E:
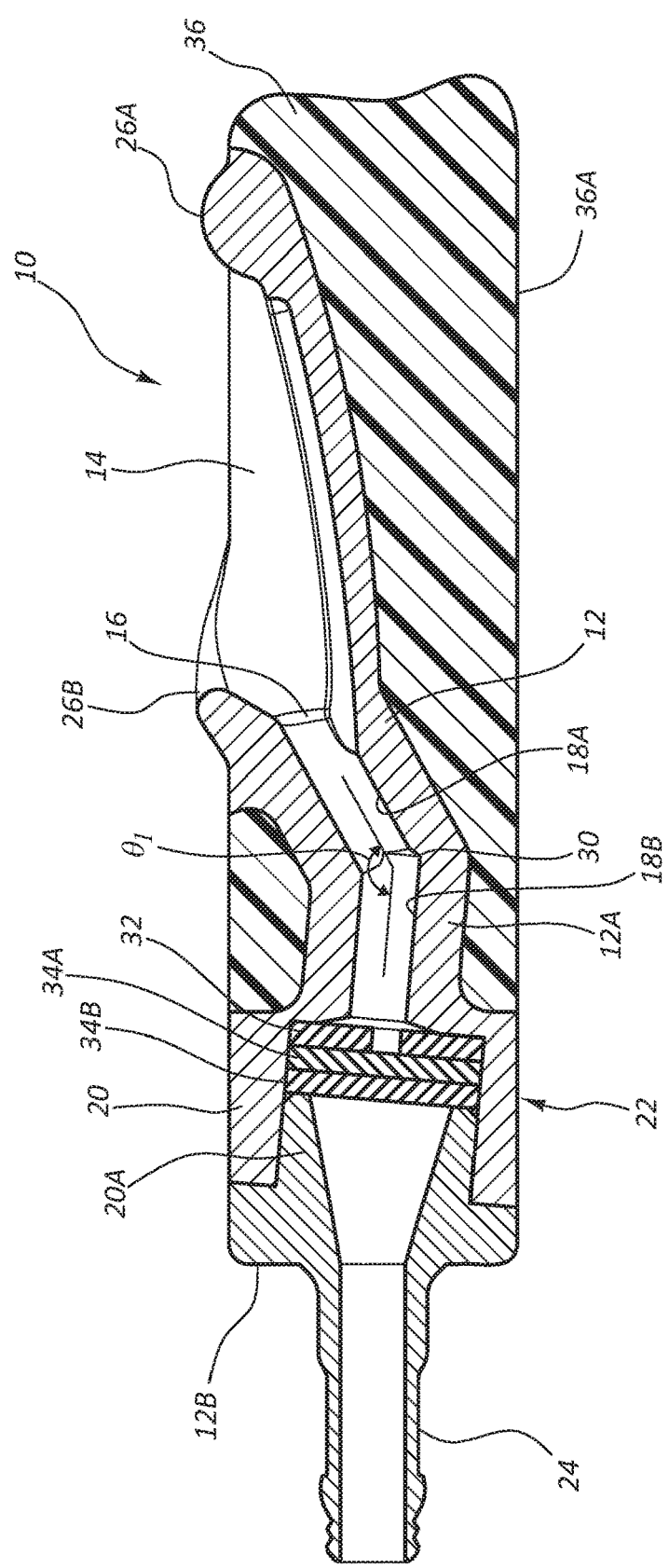

Reference is first made to made to FIGS. 1A-1E, which show various details of an access port, generally designated at 10, in accordance with one embodiment. As shown, the port 10 includes a body 12 that is defined in the present embodiment by a first portion 12A and a second portion 12B (FIG. 1E). In the present embodiment the port body 12 includes a metal such as titanium, and as such, the second portion 12B is press fit into engagement with the first portion 12A to define the body, though it is appreciated that the port body can include a variety of other materials, including metals, thermoplastics, ceramics, etc.

Figure 2:
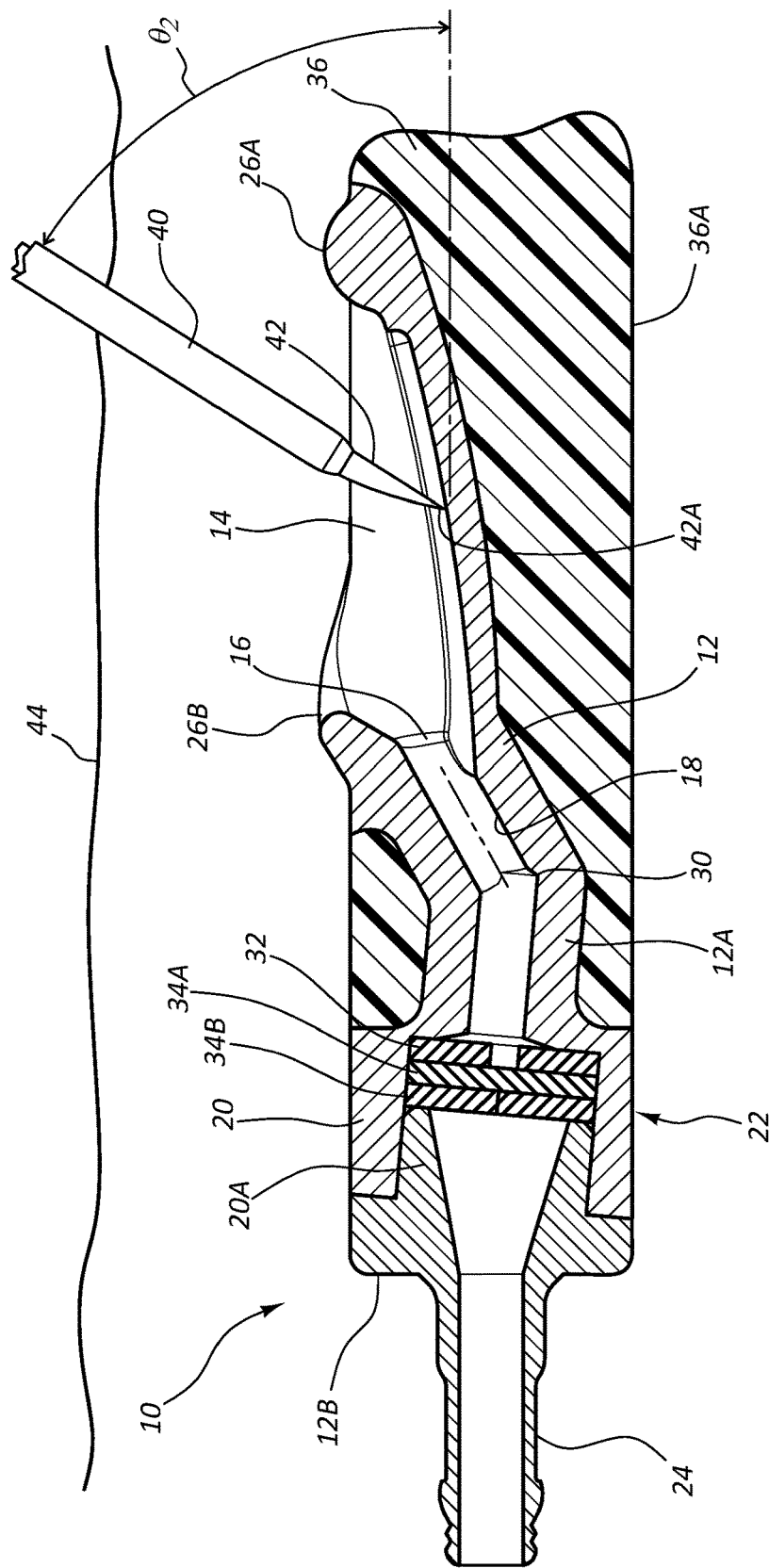
FIG. 2 is a cross sectional view of the access port of FIGS. 1A-1E.

The port body 12 defines in the present embodiment a substantially concavely-shaped receiving cup 14 for receiving and directing a catheter-bearing needle (FIG. 2) to operably connect with the port 10, as described further below. In particular, the substantially concave shape of the receiving cup 14 is configured to direct a catheter-bearing needle (FIG. 2) impinging thereon toward an inlet port 16 that serves as an opening for a conduit 18 defined by the port body 12. The open and shallow nature of the receiving cup 14 together with its substantially upward orientation (i.e., toward the skin surface of the patient), so that it is substantially parallel to the skin surface when subcutaneously implanted under the skin of the patient (i.e., the receiving cup is substantially parallel to the skin surface when the skin is at rest, or undeformed by digital pressure or manipulation), enables the receiving cup to present a large, easily accessible target for the needle when introduced into the skin, as seen in FIG. 2. FIG. 2 further shows that the port 10 defines a relatively low profile height, which enables relatively shorter needle lengths to be used for accessing the port after implantation.

Palpation features 26 are included with the port body 12 to assist a clinician to locate and/or identify the port 10 via finger palpation after implantation under the skin of the patient. In detail, the palpation features 26 in the present embodiment include a bump 26A disposed near the proximal end of the receiving cup 14 and a ridge 26B disposed above and curving around a distal portion of the receiving cup. FIG. 1B shows that the palpation features extend above the general upper plane defined by the port 10 so as to facilitate palpation of the features by a clinician in order to locate the position and/or orientation of the receiving cup 14. Note that a variety of other sizes, configurations, numbers, etc., of palpation features can be included on the port in addition to what is shown and described herein.

A guide groove 28 is defined on the receiving cup 14 and is longitudinally aligned with the inlet port 16 of the conduit 18. The guide groove 28 is defined as a depression with respect to adjacent portions of the surface of the receiving cup 14 and extends distally along the receiving cup surface from a proximal portion of the receiving cup so as to provide a guide path to guide the distal tip of the catheter-bearing needle toward the inlet port 16 once impingement of the needle into the guide groove is made. This in turn reduces the chance the needle will slide across and off the receiving cup 14 during insertion. Note that these and other similar features, though differing in shape and configuration, can also be included on the other ports disclosed herein.

As best seen in FIG. 1E, the port body 12 further defines the conduit 18 as a pathway into which a transcutaneously inserted catheter can pass so as to place the catheter in fluid communication with the port 10. As shown, the conduit 18 is in communication with the receiving cup 14 via the inlet port 16. A first conduit portion 18A of the conduit 18 distally extends from the inlet port 16 in an angled downward direction from the perspective shown in FIG. 1E to a bend 30, where a second conduit portion 18B of the conduit angles slightly upward and changes direction at a predetermined angle $\theta_1$. Note that angle orientation $\theta_1$ in one embodiment is about 37 degrees, but can vary from this in other embodiments, including angles less than 37 degrees in one embodiment. The magnitude of angle $\theta_1$ depends in one embodiment on various factors, including the size of the catheter and/or needle to be inserted into the port conduit, the size of the conduit itself, etc.

The conduit 18 then extends to and through a cavity 20A defined by a valve housing 20 of the port body. The conduit 18 extends to a distal open end of the stem 24 of the port 10. The conduit 18 is sized so as to enable the catheter 40 (FIG. 2) to pass therethrough, as will be seen.

As mentioned, the valve housing 20 defines a cavity 20A through which the conduit passes and which houses a valve/seal assembly 22. The valve/seal assembly 22 includes a sealing element, or seal 32, which defines a central hole through which the catheter 40 can pass, a first slit valve 34A and a second slit valve 34B. The seal 32 and valves 34A, 34B are sandwiched together in one embodiment and secured in place within the cavity 20A as shown in FIG. 1E. The slits of the slit valves 34A, 34B are rotationally offset from one another by about 90 degrees in the present embodiment, though other relationships are possible.

The seal 32 and valves 34A, 34B of the valve/seal assembly 22 cooperate to enable fluid-tight passage therethrough of the catheter 40 (FIG. 2) while also preventing backflow of fluid through the valve/seal assembly. Indeed, in one embodiment the seals disclosed herein prevent fluid flow around the external portion of the catheter when the catheter is disposed through the seal, while the valves are suitable for preventing fluid flow when no catheter passes through them. As such, when the catheter 40 is not inserted therethrough the valve/seal assembly 22 seals to prevent passage of air or fluid. In the present embodiment, the seal 32 and valves 34A, 34B include silicone, though other suitably compliant materials can be employed.

The port 10 in the present embodiment includes an overmolded portion 36 that covers the port body 12. The overmolded portion 36 includes silicone or other suitably compliant material and surrounds the body 12 as shown so as to provide a relatively soft surface for the port 10 and reduce patient discomfort after port implantation. The overmolded portion 36 includes two predetermined suture locations 38, best seen in FIG. 1C, for suturing the port 10 to patient tissue, though sutures may be passed through other portions of the overmolded portion, if desired. The overmolded portion 36 further defines a relatively flat bottom surface 36A so as to provide a stable surface for the port 10 in its position within the tissue pocket after implantation. In contrast, the port shown in FIG. 3C includes a bottom surface with a slightly rounded profile.

FIG. 2 depicts details regarding the insertion of the catheter 40 disposed on the needle 42, according to one embodiment. After locating the port 10 via through-skin palpation of the palpation features 26, a clinician uses the catheter-bearing needle 42 to pierce a skin surface 44 and insert the needle until a distal tip 42A thereof impinges on a portion of the receiving cup 14, as shown. Note that, because of the orientation of the receiving cup 14 as substantially parallel to the skin surface, the needle 42 can impinge on the receiving cup at an insertion angle $\theta_2$ that is relatively steep, which facilitates ease of needle insertion into the body. Indeed, in one embodiment a needle inserted substantially orthogonally through the skin of the patient can impinge the receiving cup of the access port.

The needle 42 is manipulated until the distal tip 42A is received into the guide groove 28, which will enable the distal tip to be guided along the groove to the inlet port 16. The needle 42 is then inserted through the inlet port 16 and into the first portion 18A of the conduit 18 until it is stopped by the bend 30. The needle 42 can then be proximally backed out a small distance, and the catheter 40 advanced over the needle such that the catheter bends and advances past the bend 30 into the second portion 18B of the conduit 18. Catheter advancement continues such that a distal end 40A of the catheter 40 advances into and past the hole of the seal 32 and through both slits of the slit valves 34A, 34B of the valve/seal assembly 40. Once the distal end 40A of the catheter 40 has extended distally past the valve/seal assembly 22, further advancement can cease and fluid transfer through the catheter 40 and port 10 can commence, including infusion and/or aspiration through the stem 24. Once fluid transfer is completed, the catheter 40 can be withdrawn proximally through the valve/seal assembly 22 and the conduit, then withdrawn through the surface 44 of the skin and out of the patient.

Figure 3A:
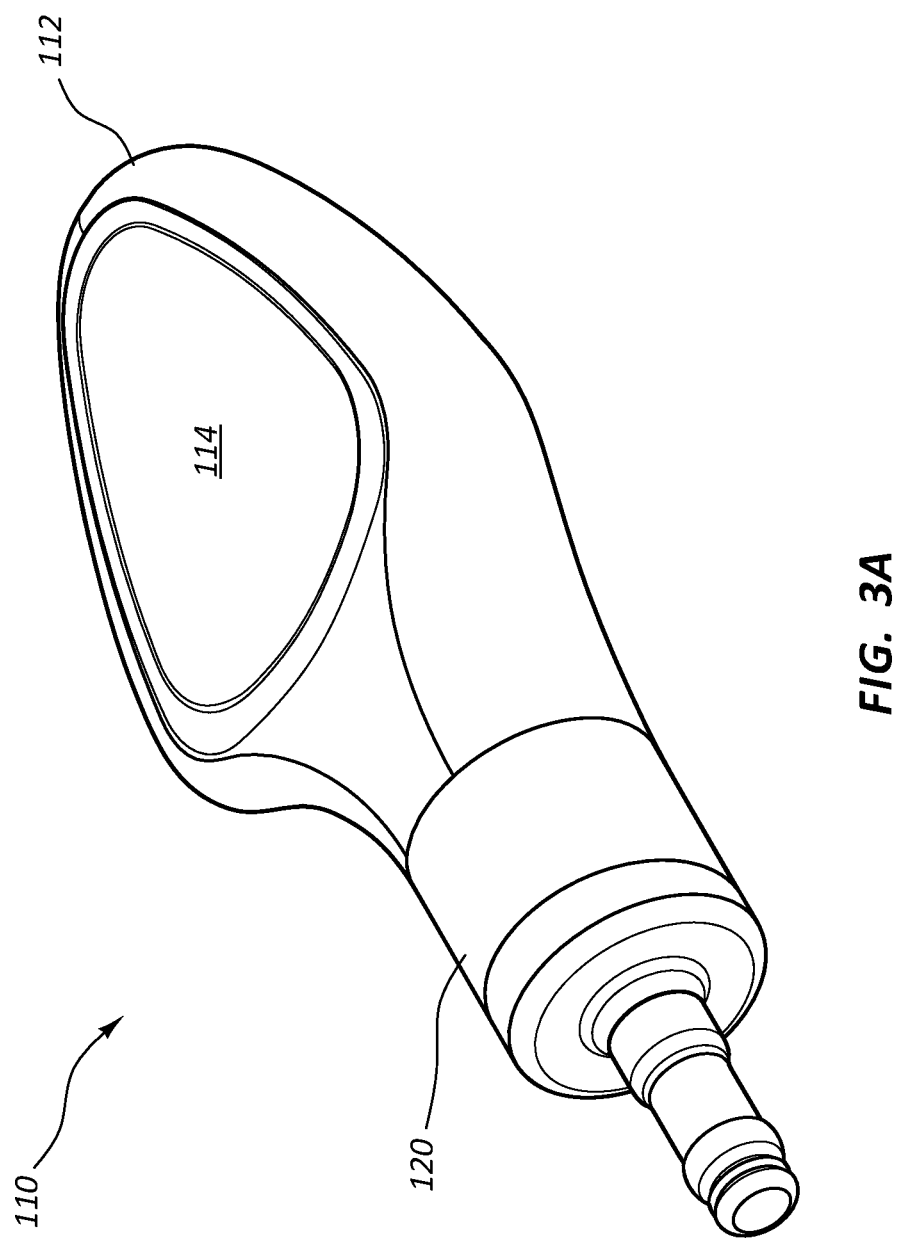
FIG. 3A-3C are various views of a low-profile access port according to one embodiment.
Figure 3B:
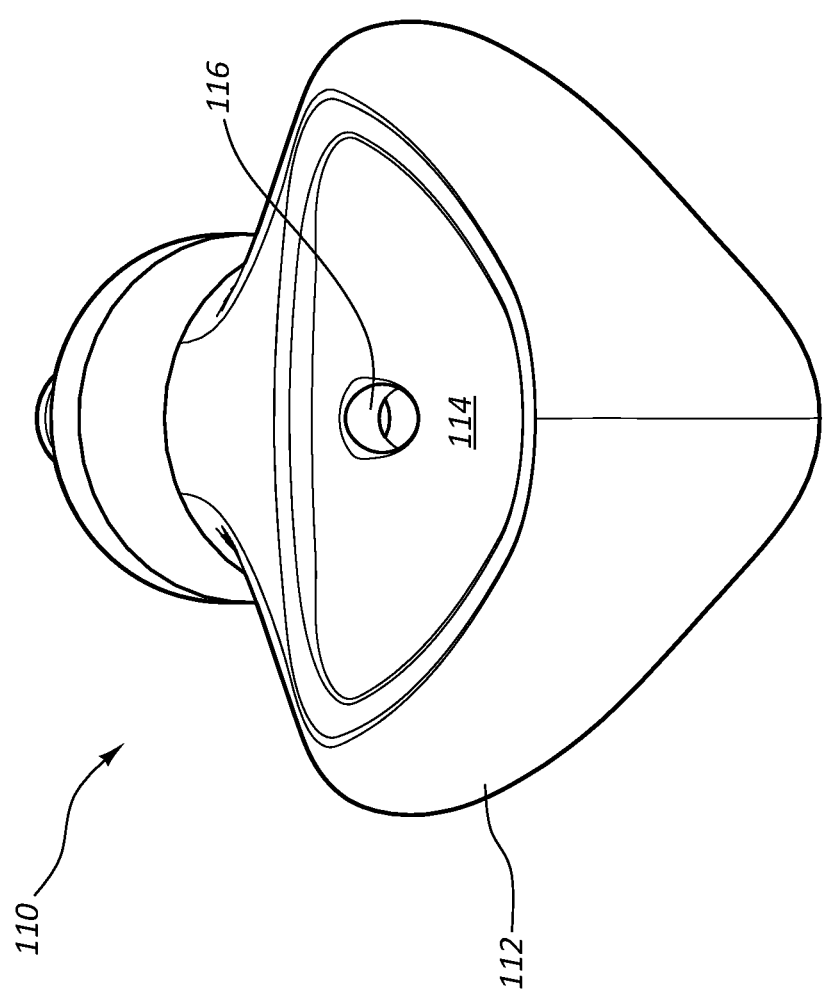
Figure 3C:
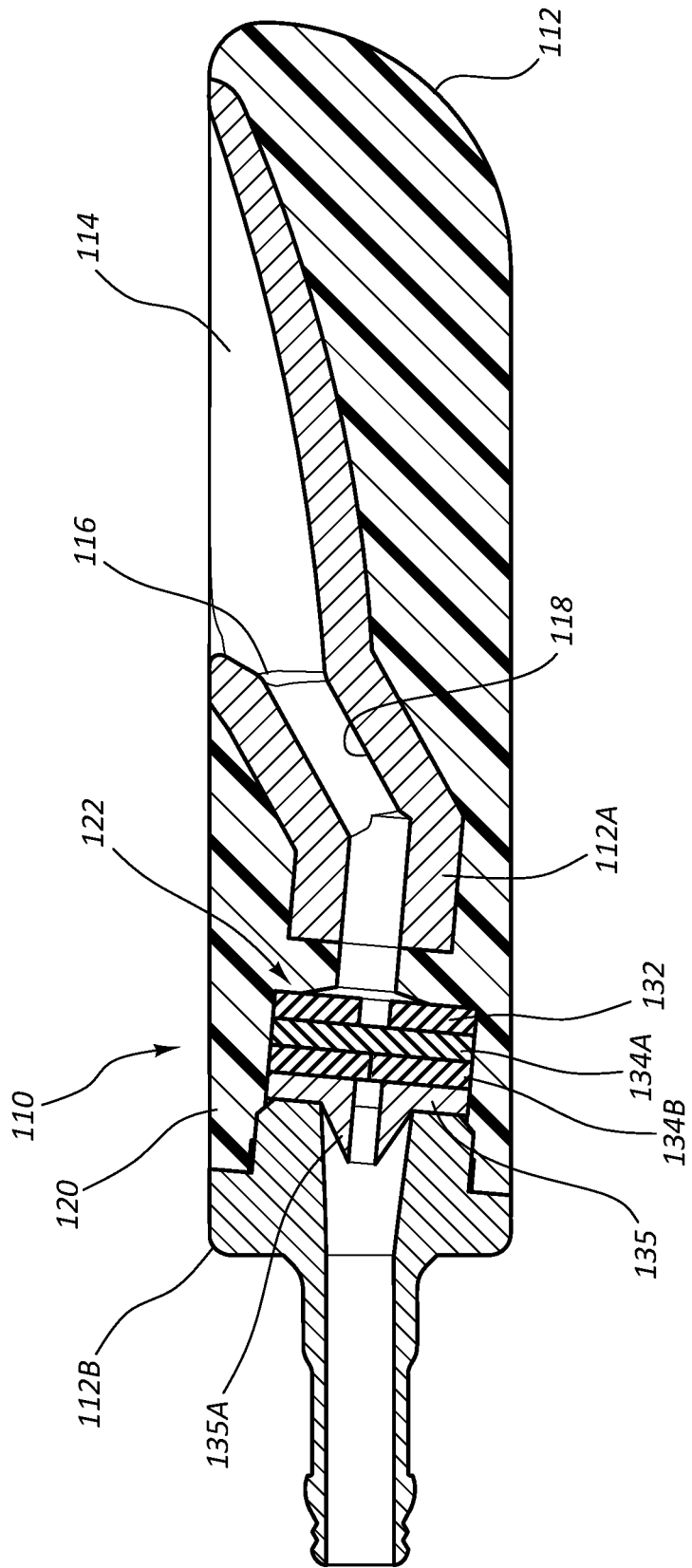

FIGS. 3A-3C depict details of an access port 110 according to another embodiment. Note that various similarities exist between the port 10 and the other ports shown and described herein. As such, only selected port aspects are discussed below. As shown, the port 110 includes a body 112 that in turn includes a first body portion 112A and a second body portion 112B, best seen in FIG. 3C. The body 112 in the present embodiment includes a thermoplastic, such as an acetyl resin in the present embodiment. As such, the first and second body portions 112A, 112B are ultrasonically welded to one another to define the body 12, in the present embodiment. As before, a receiving cup 114 is included with the body 112 and is operably connected to a conduit 118 via an inlet port 116. Also, note that a variety of materials can be used to define the port body, receiving cup, conduit, etc.

A valve/seal assembly 122 is disposed within a cavity 120A that is defined by a valve housing 120, which in the present embodiment, is defined by the first body portion 112A. The valve/seal assembly 122 includes a proximal seal 132 with a central hole for catheter passage, two slit valves 134A, 134B each with a slit arranged at a 90-degree offset with respect to the other, and a distal seal 135 with a central hole, also referred to herein as a sphincter seal.

The distal seal 135 includes on its distal surface a frustoconical portion 135A disposed about the seal central hole that is configured to provide a sphincter-like seal about the outer surface of a catheter when it extends through the valve/seal assembly. The frustoconical portion 135A is disposed such that any back-flowing fluid impinging on the frustoconical portion will cause the seal to secure itself about the outer surface of the catheter in an even tighter engagement, thus preventing backflow past the catheter outer surface when high fluid pressures are present, such as in the case of power injection. As mentioned, other valve/seal combinations can also be included in the valve/seal assembly.

In the present embodiment, the receiving cup 114 and portion of the conduit 118 proximal to the valve/seal assembly 122 both include a needle-impenetrable lining that prevents the distal end of a needle from gouging the surface when impinging thereon. This, in turn, prevents the undesirable creation of material flecks dug by the needle. Various suitable materials can be employed for the needle-impenetrable material, including glass, ceramic, metals, etc. In one embodiment, the components of the port 110 are all non-metallic such that the port is considered MRI-safe, by which the port does not produce undesired artifacts in MRI images taken of the patient when the port is in implanted therewithin.

Figure 4:
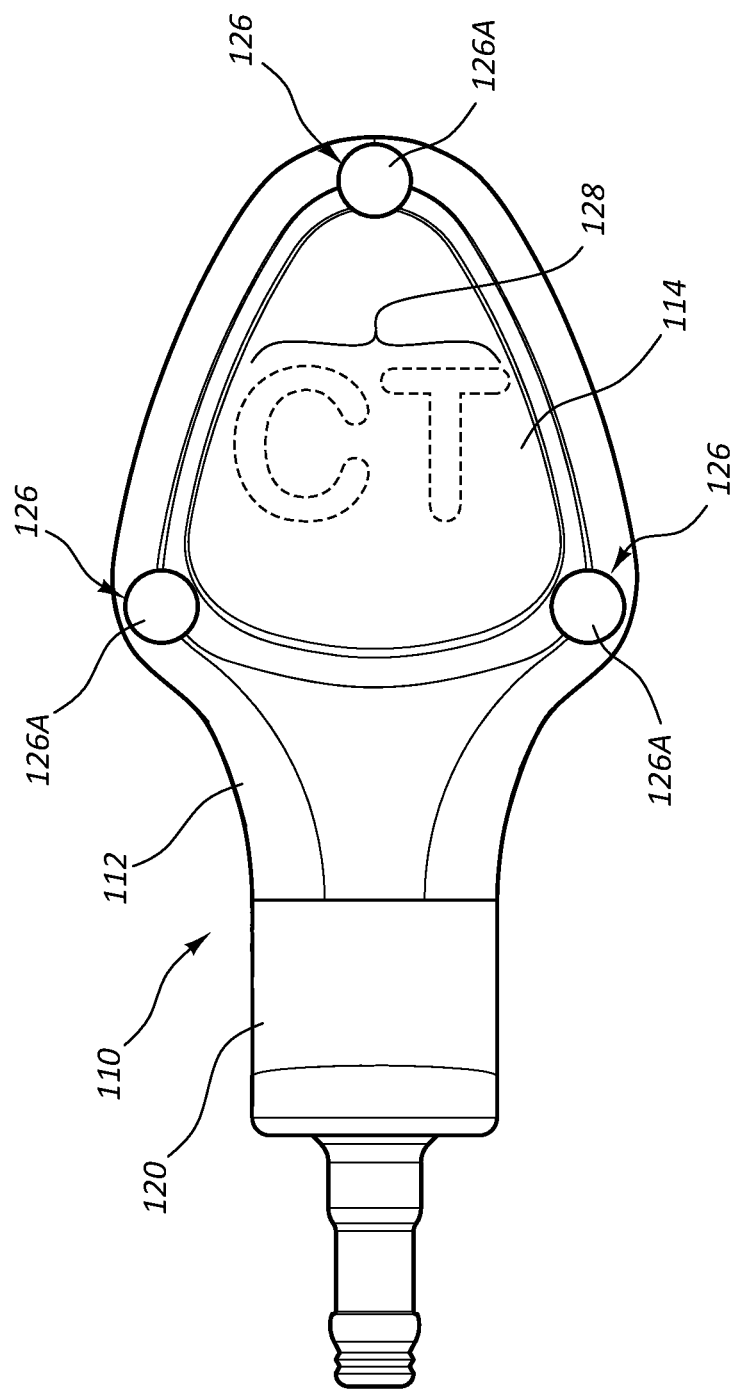
FIG. 4 is a top view of a low-profile access port according to one embodiment.

FIG. 4 depicts additional features of the port 110 according to another embodiment. As shown, in the present embodiment the receiving cup 18 includes radiopaque indicia 128 to indicate a characteristic of the port 110. Here, the radiopaque indicia 128 includes a "C" and a "T" that are formed by a radiopaque material, such as tungsten, bismuth trioxide, etc., so as to be visible after port implantation via x-ray imaging technology. For instance, the radiopaque material can be formed as an insert that is insert-molded included in the port body, as an initially flowable material that is injected into a cavity of the port body before hardening, etc. In embodiments where the port body is metallic, the radiopaque indicia can be formed by etching, engraving, or otherwise producing a relative thickness difference between the indicia and the surrounding port body material so as to produce an x-ray-discernible contrast that shows up in an x-ray image.

In the present embodiment, the CT radiopaque indicia 128 indicate to an observer that the port is capable of power injection of fluids therethrough. In addition to this characteristic, other characteristics can be indicated by various other types of indicia as appreciated by one skilled in the art.

Further, in the present embodiment the top view of the port 110 of FIG. 4 indicates that the port body 112 in the region surrounding the receiving cup 114 defines a generally triangular shape, which can be palpated by a clinician after implantation and can indicate not only the location of the receiving cup, but also a particular characteristic of the port, such as its ability to be used for power injection. Of course, the receiving cup may define shapes other than triangular in other embodiments.

FIG. 4 further shows that distributed about the perimeter of the receiving cup 114 are three palpation features 126, namely, three suture plugs 126A disposed in corresponding holes defined in the port body 112. The suture plugs 126A include raised silicone bumps in the present embodiment and can serve to locate the position of the receiving cup 114 post-implantation when they are palpated by a clinician prior to needle insertion into the patient. Various other palpation features could be included with the port, in other embodiments.

Figure 5:
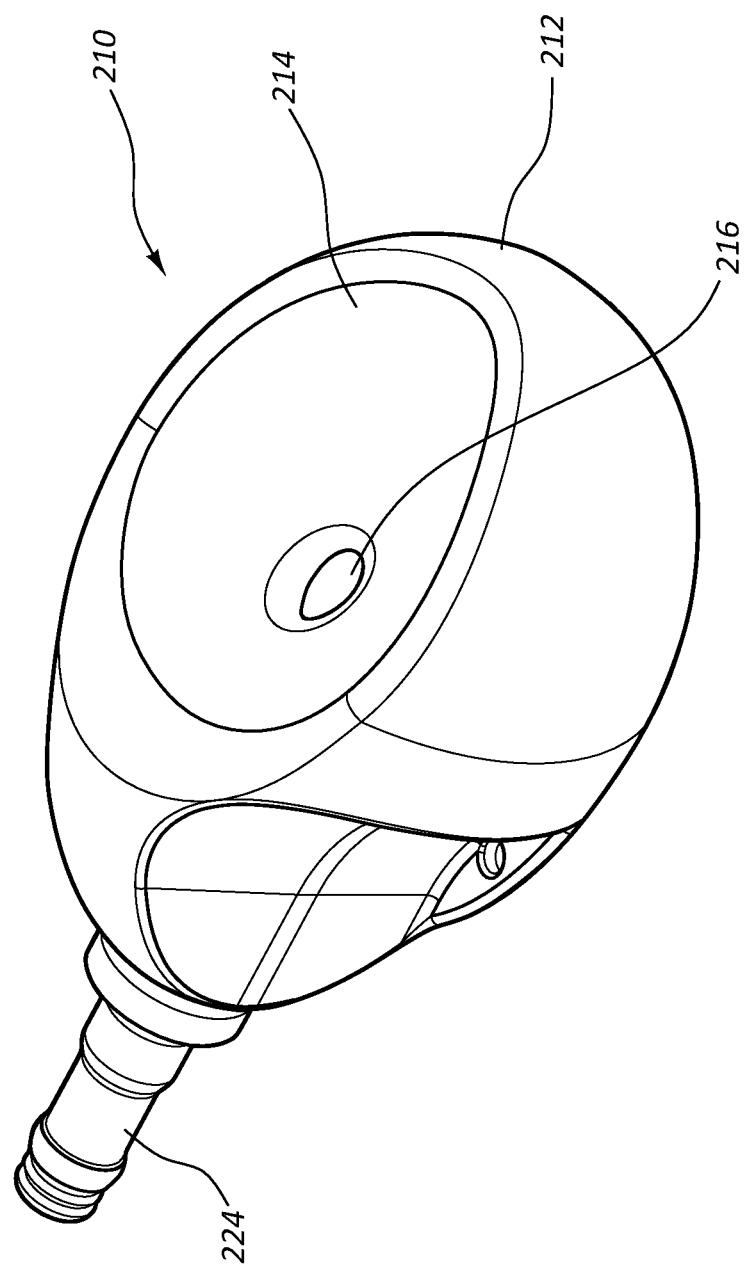
FIG. 5 is a perspective view of a low-profile access port according to one embodiment.

FIG. 5 depicts details of a low-profile port 210 according to one embodiment, including a body 212 defining a concavely-shaped receiving cup 214 and an inlet port 216 positioned slightly off-center with respect to the receiving cup. A stem 224 is included as a fluid outlet.

Figure 6:
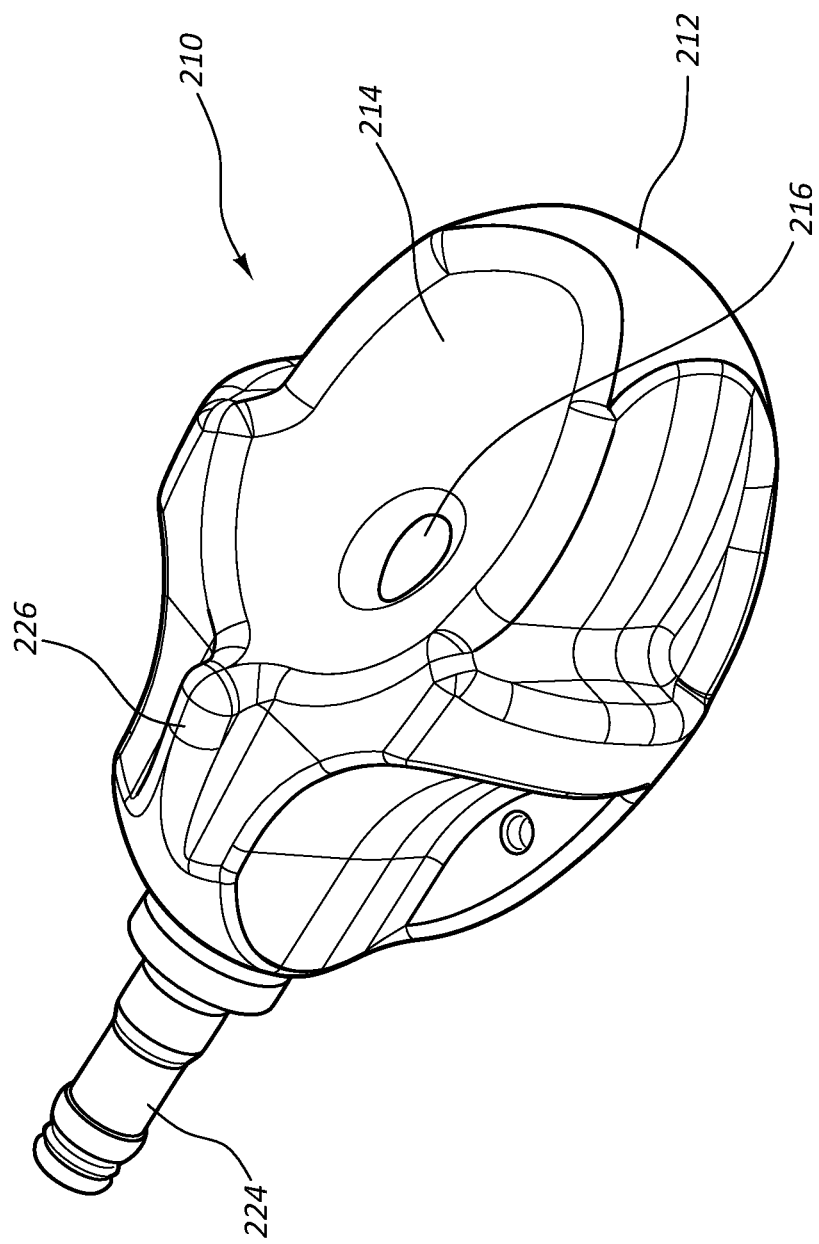
FIG. 6 is a perspective view of a low-profile access port according to one embodiment.

FIG. 6 depicts the low-profile port 210 according to another embodiment, wherein the body 212 defining additional surface features, including a raised palpation feature 226 distal to the receiving cup 214. In light of FIGS. 5 and 6, it is thus appreciated that the port can be configured in a variety of shapes and configurations to provide a low-profile solution for providing vascular access. Note also that the receiving cup shape, design, and configuration can vary from is explicitly shown and described herein.

Figure 7A:
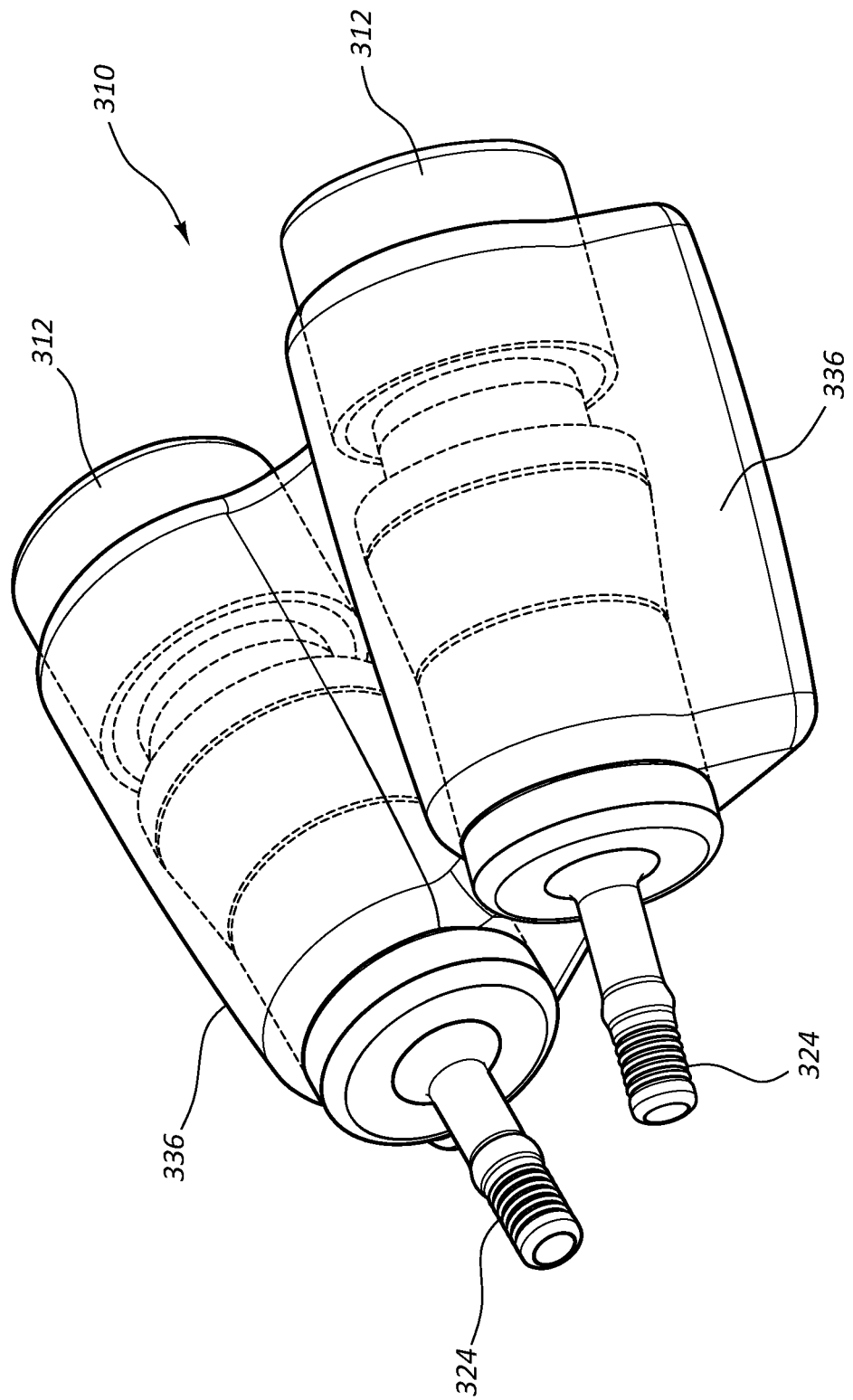
FIGS. 7A and 7B are various views of an access port according to one embodiment.
Figure 7B:
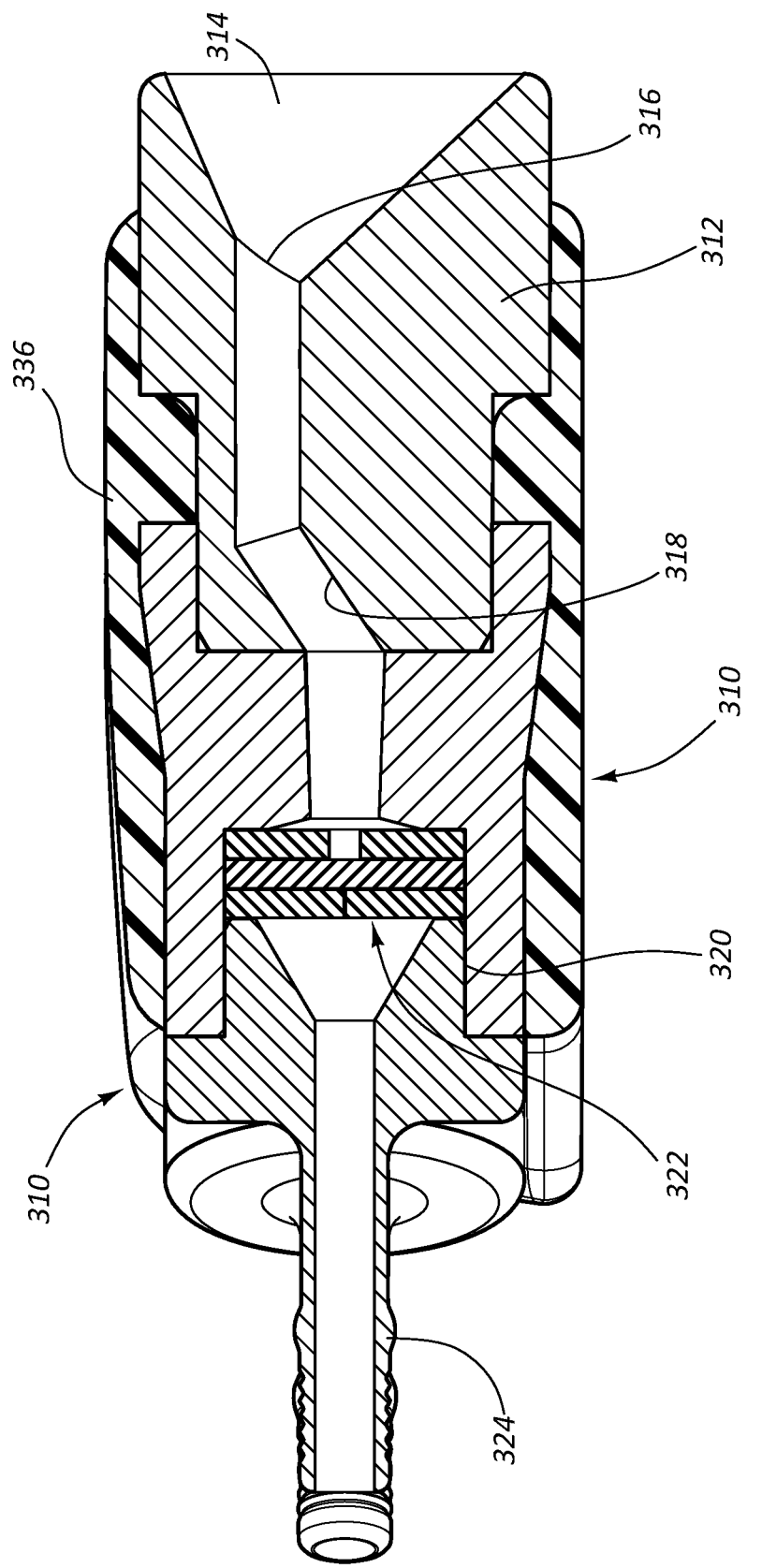

FIGS. 7A and 7B depict various details of a low-profile dual-body access port 310 according to one embodiment, wherein each of the port bodies 312 defines a receiving cup 314 that is laterally facing and includes an inlet port 316 leading to a conduit 318. The conduit 318 extends distally to a valve/seal assembly 322 disposed in a valve housing 320, which in the present embodiment, is defined by a portion of the body 312. The conduit 318 extends through the port 324. A compliant overmolded portion 324 covers portions of each body 312 of the port 310 and operably joins the bodies to one another. The bodies 312 can include any suitable material, including metal, thermoplastic, etc.

Figure 8A:
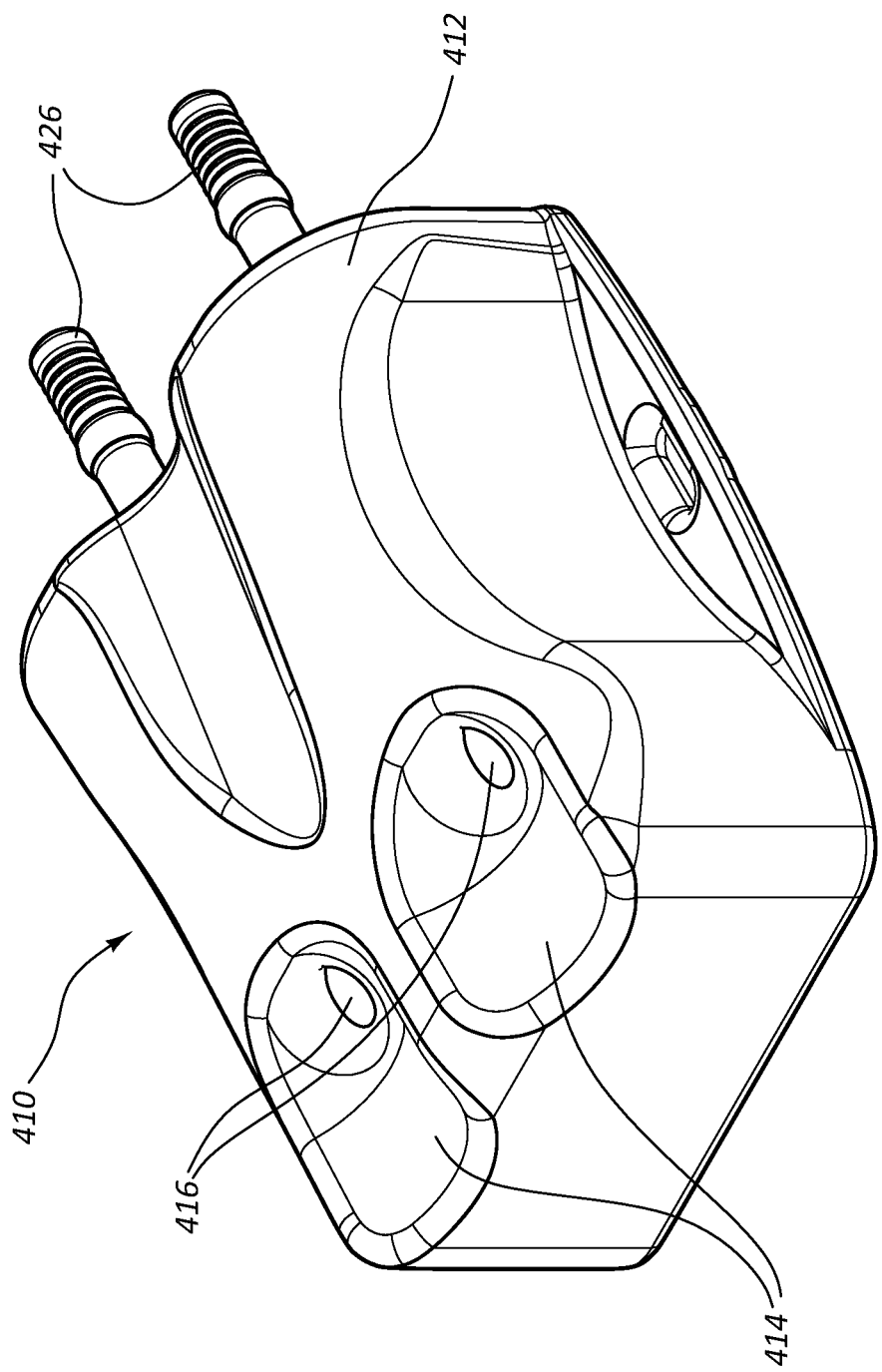
FIGS. 8A and 8B are various views of an access port according to one embodiment.
Figure 8B:
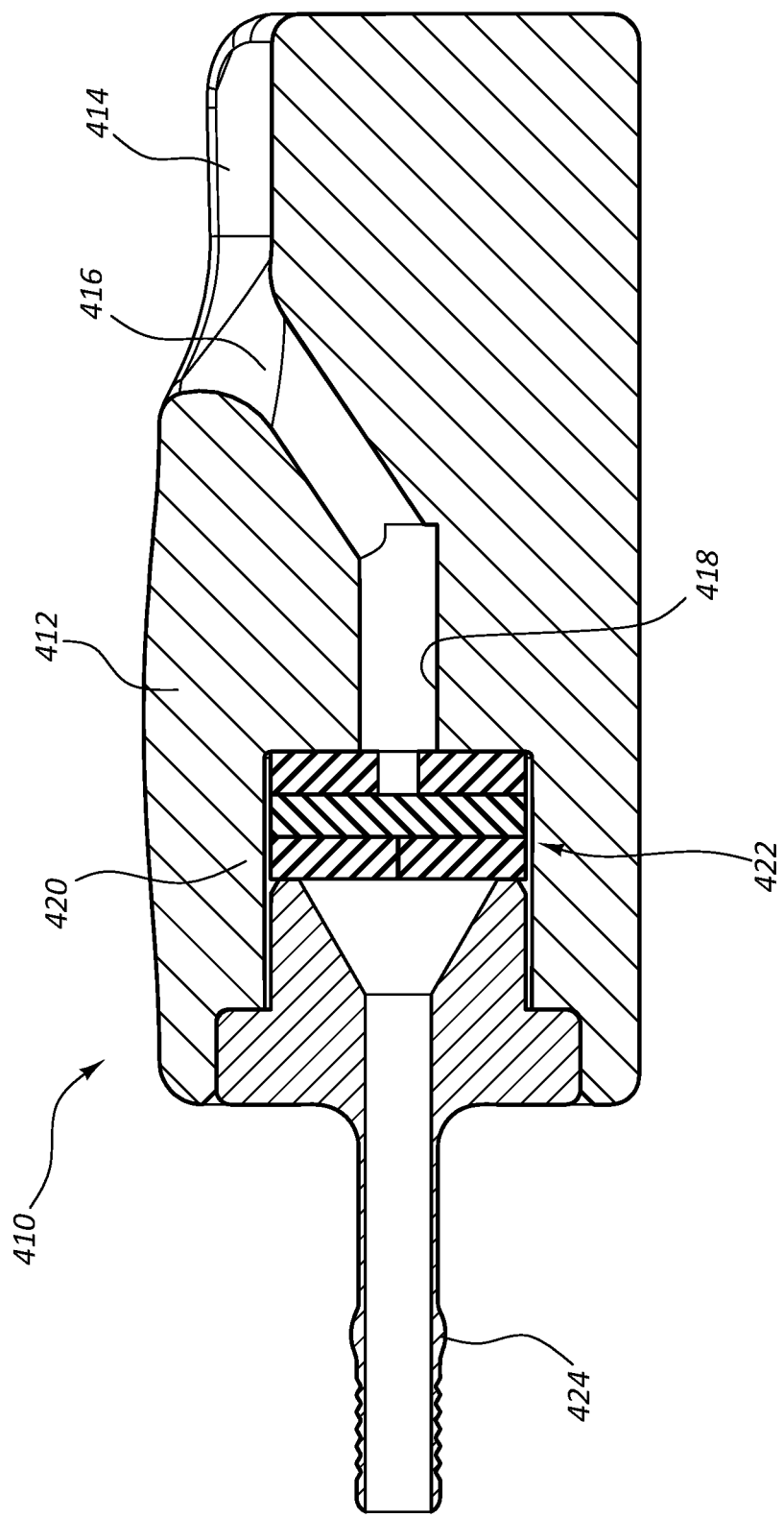

FIGS. 8A and 8B depict various details of a low-profile dual-body access port 410 according to one embodiment, wherein a port body 412 defines dual fluid paths. Each fluid path includes a receiving cup 414 defined by the body 412 and facing a substantially upward orientation from the perspective shown in FIGS. 8A and 8B. An inlet port 416 is included with each receiving cup 414 and defines the opening to a conduit 418. Each conduit 418 extends distally to a valve/seal assembly 422 disposed in a valve housing 420, which in the present embodiment, is defined by a portion of the body 412. The conduit 418 extends through the port 424. The body 412 can include any suitable material, including metal, thermoplastic, etc.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A low-profile access port for subcutaneous placement in a patient, comprising:
   a body including:

a conduit;
a receiving cup including:
a concavely shaped surface having a length greater than a width;
an upper opening lying in an upper plane;
a lower opening in communication with the conduit; and
a single guide groove defining a depression in the concavely shaped surface along the length from a proximal portion of the receiving cup to the lower opening to redirect an impinging distal tip of a needle into the conduit via the lower opening; and
a palpation bump positioned at a proximal end of the receiving cup, the palpation bump extending through the upper plane; and
a valve/seal assembly disposed in the conduit that enables passage of a catheter therethrough.

2. The access port as defined in claim 1, wherein the conduit includes a first conduit portion and a second conduit portion, the second conduit portion positioned distal to and at an angled orientation with respect to the first conduit portion.

3. The access port as defined in claim 2, wherein the second conduit portion is disposed at an angle less than about 37 degrees with respect to the first conduit portion.

4. The access port as defined in claim 1, wherein the upper plane is positioned substantially parallel to a skin surface when the access port is subcutaneously implanted.

5. The access port as defined in claim 1, wherein the conduit includes a first portion in communication with the lower opening and a second portion in communication with the first portion, wherein the first portion is angled toward a bottom surface of the access port, and wherein the second portion is angled toward a top surface of the access port.

6. The access port as defined in claim 1, further comprising a stem having a proximal portion positioned within a distal cavity of the body, the proximal portion of the stem including an inlet in communication with the valve/seal assembly.

7. The access port as defined in claim 1, further comprising a palpation ridge disposed opposite the palpation bump on the receiving cup.

8. The access port as defined in claim 7, wherein the palpation ridge extends over the upper opening and the lower opening of the receiving cup.

9. The access port as defined in claim 1, further comprising a housing surrounding the body, the housing forming a top surface and a bottom surface of the access port.

10. The access port as defined in claim 9, wherein the bottom surface is flat, and wherein the bottom surface is parallel to the top surface.

11. The access port as defined in claim 1, wherein the valve/seal assembly includes a first seal, a first slit valve, and a second slit valve positioned in a sandwiched configuration with respect to one another.

12. The access port as defined in claim 1, wherein at least a portion of the receiving cup includes a needle-impenetrable material.

13. The access port as defined in claim 12, wherein the needle-impenetrable material includes at least one of metal, glass, and ceramic.

14. The access port as defined in claim 1, wherein the body includes at least one of a metal and a thermoplastic.

15. The access port as defined in claim 14, wherein at least a portion of the body includes at least one of titanium and acetyl resin.

16. The access port as defined in claim 15, wherein the palpation bump includes a portion on the concavely shaped surface proximal of the guide groove that is substantially centered in the receiving cup.

17. A method for manufacturing a low-profile access port for subcutaneous placement in a patient, the method comprising:
providing a body defining a conduit, the body including:
a receiving cup defining an upper opening and a concavely shaped surface, the upper opening lying in an upper plane, the receiving cup including:
a lower opening in communication with the conduit; and
a single guide groove defining a depression in the concavely shaped surface to direct an impinging distal tip of a catheter-bearing needle into the conduit via the lower opening; and
a distal cavity in communication with the conduit;
overmolding a silicone housing around the body to form a top surface and a bottom surface of the low-profile access port, wherein the bottom surface is parallel to the upper plane;
placing a valve/seal assembly in the distal cavity; and
inserting a proximal end of a stem into the distal cavity to capture the valve/seal assembly in the body between the conduit and the stem.

18. A low-profile access port for subcutaneous placement in a patient, comprising:
a body including:
a conduit;
a receiving cup including:
a concavely shaped surface having a length greater than a width;
an upper opening lying in an upper plane;
a lower opening in communication with the conduit; and
a guide groove defining a depression in the concavely shaped surface along the length from a proximal portion of the receiving cup to the lower opening to guide a distal tip of a needle toward the lower opening; and
a palpation bump positioned at a proximal end of the receiving cup, the palpation bump extending above the upper plane; and
a valve/seal assembly in communication with the conduit that enables passage of a catheter therethrough, and including at least one seal for preventing backflow through the valve/seal assembly.

19. The access port as defined in claim 18, further comprising a palpation ridge disposed opposite the palpation bump on the receiving cup.

20. The access port as defined in claim 19, wherein the at least one seal defines a central hole therethrough and wherein a distal face of the at least one seal includes a frustoconical portion disposed about the central hole for preventing backflow past the catheter when fluid is passed through the catheter under pressure.

21. The access port as defined in claim 20, wherein the upper plane is oriented substantially toward a skin surface when subcutaneously implanted within the patient, and wherein a compliant overmolded portion surrounds the body of the access port.

22. The access port as defined in claim 21, wherein the overmolded portion includes at least one predetermined region through which sutures can be passed to secure the access port to tissue of the patient.

23. The access port as defined in claim 22, wherein the valve/seal assembly further includes first and second slit valves that are sandwiched between the at least one seal and a second seal.

* * * * *